United States Patent [19]
Holstein et al.

[11] Patent Number: 5,259,383
[45] Date of Patent: Nov. 9, 1993

[54] STERILE ULTRASOUND COVER TUBE

[75] Inventors: Klaus Holstein, Hamburg; Olaf Lehmann, Tangstedt; Robert Hebel, Erlangen; Karl-Jürgen Schmitt, Bamberg, all of Fed. Rep. of Germany

[73] Assignees: Johnson & Johnson Medical, Inc., N.J.; Siemens Aktiengesellschaft, Fed. Rep. of Germany

[21] Appl. No.: 757,794

[22] Filed: Sep. 11, 1991

[51] Int. Cl.$^5$ ............................. A61B 8/00; A61B 8/12
[52] U.S. Cl. ............................. 128/660.01; 128/662.03; 128/662.06
[58] Field of Search ............... 128/660.01, 662.03, 128/662.06, 663.01, 855, 856

[56] References Cited

U.S. PATENT DOCUMENTS

| | | | |
|---|---|---|---|
| 4,593,699 | 6/1986 | Poncy et al. | 128/662.03 |
| 4,722,346 | 2/1988 | Chen | 128/662.03 |
| 5,010,900 | 4/1991 | Auchinlech et al. | 128/855 |

OTHER PUBLICATIONS

Duff, P. et al "An Important Medical Use for the Baggie", NEJM Dec. 26, 1986 p. 1681.

*Primary Examiner*—Francis Jaworski

[57] ABSTRACT

Sterile cover tube for the transducer and connection cable of a medical ultrasound unit, in particular for intracorporeal or intraoperative sonography. The cover tube consists of a plastic foil tube (10) whose one end (11) is closed and is at least as long as the transducer and a connection cable part. The plastic foil tube is arranged ready for use in a telescopic folding (14 to 20). The closed tube end (11) projects into the telescopic folding by a length which is smaller than the length of the remaining telescopic folding (15 to 20) overlying the closed end on the outside. The sterile covering of the ultrasound head and of the connection cable of the ultrasound unit requires only two people. The plastic foil tube is suitable for all sonographic ultrasound probes. Coupling agents can be introduced into the closed tube end without any problem.

11 Claims, 1 Drawing Sheet

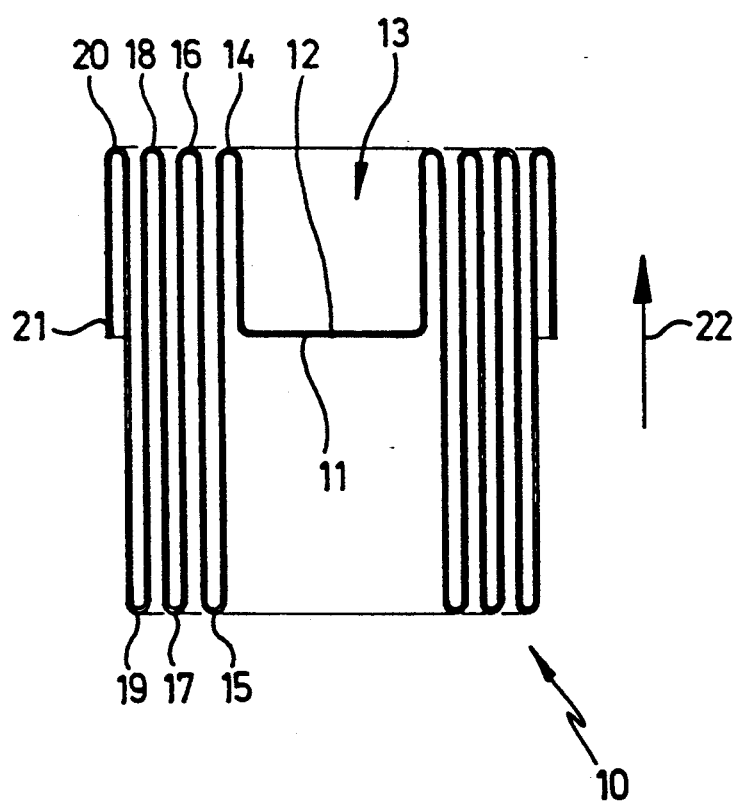

STERILE ULTRASOUND COVER TUBE

The invention relates to a sterile cover tube for the transducer and the connection cable of a medical ultrasound unit, in particular for intracorporeal or intraoperative sonography.

This type of sterile covering is described in detail in an article "Sonographie in der Allgemeinchirurgiell (Sonography in General Surgery) in the periodical Electromedica (1989) 57, volume 4, and the individual steps for sterile covering of an ultrasound probe are illustrated. According to this, a non-sterilizable probe with cable is first inserted into a sterile plastic tube which covers the whole cable right up to the connector. The ultrasound head itself is then glued over with a sterile operation foil and secured with a sterile OP tape. Three people are needed for the preparatory measures for the sterile covering. In addition, the operation foil on the probe must be applied in the area of the ultrasound transducer in a manner absolutely free from air, since otherwise artifacts impair the quality of the ultrasound image.

The invention is based on the object of improving a sterile cover tube of the known generic type mentioned at the outset in such a way that a simple and reliable handling is guaranteed with a sterile covering of the ultrasound head and of the connection cable of the ultrasound unit.

The invention achieves this object by virtue of the fact that the cover tube consists of a plastic foil tube which is closed at one end and has a length corresponding at least to the length of the transducer and a part of its connection cable, and that the plastic foil tube is arranged ready for use in a telescopic folding, in which the closed end of the plastic foil tube projects into the telescopic folding by a length which is dimensioned smaller than the length of the remaining telescopic folding overlying the closed end on the outside.

In this way, only two people are needed for complete, sterile covering of the ultrasound head or the ultrasound probe and of the associated connection cable. The plastic foil tube is suitable for all ultrasound probes used in intraoperative or intracorporeal sonography, since the first inner folding with the closed tube end projects into the telescopic folding only by a short length. Thus, an ultrasonic gel or a physiological saline solution can be introduced without problems as coupling agents into the closed tube end. Furthermore, the ultrasound probes varying in shape and size can be easily positioned, and the subsequent covering of the probe and of the connection cable can be carried out under aseptic conditions.

The closed end of the plastic foil tube is advantageously welded, the weld seam lying inside in the direction of the introduction or feed opening of the foil tube. This ensures that, when the ultrasound covering is in use, the weld seam always lies on the inside, and no possibly sharp-edged parts of the tube can appear during medical use.

For improved securing of the probes situated in the covering, it is possible to use, if appropriate, sterile OP adhesive strips or, for example, sterile, stretchable rubber rings which are pulled over the covering.

For the ultrasound covering, such plastic foils can be used as have a sufficient strength and stability at a low material thickness. The thickness and the composition of the plastic foils have a direct influence on the emitted and reflected ultrasound pulses.

An important parameter for the selection of suitable plastic foils is their acoustic impedance, that is the intrinsic impedance of the foil acting counter to the ultrasound. In terms of composition and thickness, only those foils are considered, whose impedance is almost identical to that of the tissue to be exposed to ultrasound, i.e. the foil must have an acoustic impedance of approximately $1.6 \times 10^6$ Ns/m$^3$. Only if the impedance difference between the ultrasound-conducting medium, that is to say the foil, and the echo-producing structure is very small are there no losses in the quality of the ultrasound image. Materials which satisfy the above-mentioned conditions, that is to say sufficient stability and strength with a low material thickness and suitable acoustic impedance, are in particular radiosterilizable plastic foils of high-density and low-density polyethylene and copolymers of ethyl/butyl acrylate or ethylene/methyl acrylate (EMA) in a material thickness of 15 $\mu$m to 50 $\mu$m, but of course other materials too which, with low thickness and appropriate impedance values, have moreover the necessary stability.

The invention is described hereinbelow with reference to the diagrammatic drawing of an exemplary embodiment of a sterile plastic foil tube designed as a ready to use sterile covering, consisting of telescopic foldings, for intraoperative or intracorporeal sonography. A plastic foil tube 10 consists of a highpressure polyethylene foil whose thickness is 25 $\mu$m. The foil tube has a diameter of 14 cm and a total length of 2.5 m. The inner end 11 of the foil tube 10 is closed by means of a weld or sealing seam 12. The sealing seam 12 lies on the inside and is therefore directed towards the introduction or feed opening 13, which is used for receiving an ultrasound head or a corresponding probe and an ultrasound gel or a physiological saline solution as coupling agents (not shown). The closed end 11 forms a first folding 14 and projects only by a length of approximately 10 cm into the following seven telescopic foldings 15, 16, 17, 18, 19, 20 which are approximately of identical length and mutually superimposed essentially radially to the longitudinal axis of the foil tube 10, whereas the subsequent foldings have a length of approximately 25 cm. It will be understood that the number and length of the foldings can be altered as desired. The outer open end 21 lies at approximately the same level as the inner closed end 11 and points counter to the direction of unfolding characterized by an arrow 22. The plastic foil tube is packed singly and flat in this telescopic folding and is offered ready for use in a hermetically sealed package which is sterilized by means of gamma rays.

We claim:

1. Sterile assembly for use with a medical ultrasound unit intended particular for intracorporeal or intraoperative sonography of a type having a transducer and a connection cable leading away from it, comprising a sealed sterile package containing a plastic foil tube (10) which is closed at one end (11), has a length corresponding at least to the length the transducer and a part of its connection cable, and is arranged in a telescopic folding (14 to 20) that has a predetermined length, in which the closed end (11) of the plastic foil tube (10) projects into the telescopic folding by a distance that is less than the length of the telescopic folding.

2. Sterile cover according to claim 1, characterized in that the distance the closed end (11) of the plastic foil tube (10) projects into the telescopic folding is less than half the length of the telescopic folding.

3. Sterile cover tube according to claim 2, characterized in that the length of the telescopic folding is approximately 25 cm and the closed end (11) of the plastic foil tube projects about 10 cm inside the telescopic folding.

4. Sterile cover tube according to claim 1, characterized in that tee closed end (11) of the plastic foil tube is welded, forming a weld seam (12) lying inside in the direction of an introduction or feed opening (13) of the telescopic folding (14 to 20) for the transducer.

5. Sterile cover tube according to claim 1, characterized in that the plastic foil for the cover tube has an acoustic impedance of approximately $1.6 \times 10^6$ Ns /m$^3$.

6. Sterile cover tube according to claim 1, characterized in that the tube comprises high-density or low-density polyethylene.

7. Sterile cover tube according to claim 1, characterized in that the tape comprises a copolymer of ethyl butyl acrylate.

8. Sterile cover tube according to claim 1, characterized in that the tube comprises a copolymer of ethylene/methyl acrylate.

9. Sterile cover tube according to claim 1, characterized in that the tube comprises of a high-pressure polyethylene foil with a thickness of 25 μm, the tube having a diameter of 14 cm and a total length of approximately 2.5 m.

10. Sterile cover tube according to claim 1, characterized in that the tube is sterilized by means of gamma rays.

11. A method for sterile covering of a medical ultrasound probe and associated cable comprising the steps of
   a) providing the sterile assembly of claim 1,
   b) introducing a coupling agent into the closed end (11) of the tube (10),
   c) positioning the probe in the closed end of the tube, and
   d) unfolding the tube to cover the probe and connecting cable under aseptic conditions.

* * * * *